(12) United States Patent
del Campillo et al.

(10) Patent No.: US 7,888,556 B2
(45) Date of Patent: Feb. 15, 2011

(54) ROOT CAP SPECIFIC PROMOTER AND METHODS OF USE IN PLANTS

(75) Inventors: Elena del Campillo, Edgewater, MD (US); Damian Crawford, Boston, MA (US)

(73) Assignee: University of Maryland, College Park, MD (US)

( * ) Notice: Subject to any disclaimer, the term of this patent is extended or adjusted under 35 U.S.C. 154(b) by 754 days.

(21) Appl. No.: 11/218,295

(22) Filed: Sep. 1, 2005

(65) Prior Publication Data

US 2007/0050862 A1    Mar. 1, 2007

(51) Int. Cl.
    C12N 15/82    (2006.01)
    C12N 15/87    (2006.01)
    A01H 1/00     (2006.01)
    C07H 21/04    (2006.01)
(52) U.S. Cl. .................. 800/287; 800/278; 536/24.1
(58) Field of Classification Search ............... None
    See application file for complete search history.

(56) References Cited

U.S. PATENT DOCUMENTS 5,401,836 A * 3/1995 Baszczynski et al. ...... 536/24.1
2003/0074698 A1 * 4/2003 Schmulling et al.

OTHER PUBLICATIONS

Kim et al. 1994, Plant Molecular Biology 24: 105-117.*
Federspiel et al. 1997, GenBank Accession No. AF000657.*
Campillo et al. 2004, Plant Molecular Biology 56:309-323.*
TAIR microarray expression search result Jan. 2005, pp. 1-3.*
Zaid A., Hughes, H.G., Porceddu, E. & Nicholas, F., Glossary of biotechnology and genetic engineering (1999). *FAO Research and Technology Paper 7*. Rome: Food and Agriculture Organization of the United Nations.*
Iijima, Morio, et al., "Root Cap Removal Increases Root Penetration Resistance in Maize (*Zea mays* L.)," *J. Experimental Botany*, 54(390): 2105-2109 (2003).
Bengough, A.G. and McKenzie, B.M., "Sloughing of Root Cap Cells Decreases the Frictional Resistance to Maize (*Zea mays* L.) Root Growth," *J. Experimental Botany*, 48(309): 885-893 (1997).
Bent, Andrew F., "Arabidopsis in Planta Transformation. Uses, Mechanisms, and Prospects for Transformation of Other Species," *Plant Physiol.*, 124: 1540-1547 (2000).
Lashbrook, Coralle C., et al., "Two Divergent Endo-β-1,4-glucanase Genes Exhibit Overlapping Expression in Ripening Fruit and Abscising Flowers," *The Plant Cell*, 6: 1485-1493 (1994).
Miyasaka, Susan C. and Hawes, Martha C., "Possible Role of Root Border Cells in Detection and Avoidance of Aluminum Toxicity," *Plant Physiology*, 125: 1978-1987 (2001).
Nicol, Frédéric, et al., "A Plasma Membrane-Bound Putative Endo-1,4-β-D-Glucanase is Required for Normal Wall Assembly and Cell Elongation in *Arabidopsis*," *The EMBO Journal*, 17(19): 5563-5576 (1998).
Tucker, Mark L., et al., "Bean Abscission Cellulase," *Plant Physiol.*, 88: 1257-1262 (1988).

Alonso, José M., et al., "Genome-Wide Insertional Mutagenesis of *Arabidopsis thaliana*," *Science*, 301: 653-657 (2003).
Birnbaum, Kenneth, et al., "A Gene Expression Map of the *Arabidopsis* Root," *Science*, 302: 1956-1960 (2003).
Borderies, Gisèle, et al., "Proteomics of Loosely Bound Cell Wall Proteins of *Arabidopsis thaliana* Cell Suspension Cultures: A Critical Analysis," *Electrophoresis*, 24: 3421-3432 (2003).
Hawes, M.C., et al., "Function of Root Border Cells in Plant Health: Pioneers in the Rhizosphere," *Annu. Rev. Phytopathol.*, 36: 311-327 (1998).
Kalaitzis, Panagiotis, et al., "Molecular Characterization of a Tomato Endo-β-1,4-Glucanase Gene Expressed in Mature Pistils, Abscission Zones and Fruit," *Plant Cell Physiol.*, 40(8): 905-908 (1999).
Del Campillo, Elena, "Multiple Endo-1,4-β-D-glucanase (Cellulase) Genes in *Arabidopsis*," *Current Topics in Developmental Biology*, 46: 39-61 (1999).
Del Campillo, Elena and Lewis, Lowell N., "Occurrence of 9.5 Cellulase and Other Hydrolases in Flower Reproductive Organs Undergoing Major Cell Wall Disruption," *Plant Physiol.*, 99: 1015-1020 (1992).
Gonzalez-Bosch, Carmen, et al., "Immunodetection and Characterization of Tomato Endo-β-1,4-Glucanase Cell Protein in Flower Abscission Zones," *Plant Physiol.*, 114: 1541-1546 (1997).
Lu, G. and Ferl, R., "An Arabidopsis cDNA Encoding Beta-Glucanase," *Plant Mol. Biol.*, 29: 883 (1995).
Wen, Fushi, et al., "Effect of Pectin Methylesterase Gene Expression on Pea Root Development," *The Plant Cell*, 11: 1129-1140 (1999).
del Campillo, Elena and Bennett, Alan B., "Pedicel Breakstrength and Cellulase Gene Expression during Tomato Flower Abscission," *Plant Physiol.*, 111: 813-820 (1996).
Thoma, Sharon L., et al., "Analysis of an Abscission-Associated Cellulase in *Arabidopsis*," University of Wisconsin, Madison WI (139), (2003).
Hawes, M.C., "Living Plant Cells Released from the Root Cap: A Regulator of Microbial Populations in the Rhizosphere?" *Plant and Soil*, 129: 19-27 (1990).
del Campillo, Elena, et al., "Root Cap Specific Expression of an endo-β-1, 4- D-glucanase (cellulase): a New Marker to Study Root Development in *Arabidopsis*," *Plant Molecular Biology*, 56: 309-323 (2004).

* cited by examiner

*Primary Examiner*—Li Zheng
(74) *Attorney, Agent, or Firm*—Darlene A. Vanstone; Carolyn S. Elmore; Elmore Patent Law Group PC

(57) ABSTRACT

The invention provides an AtCel5 promoter isolated from *Arabidopsis thaliana* that is expressed exclusively in root cap cells of both primary and secondary roots. AtCel5 is believed to be a soluble and secreted protein that plays a role in the sloughing of root cap cells from the root tip. The sloughing of root cap cells from the root tip is important because it assists the growing root in penetrating the soil. The AtCel5 gene promoter provides a new molecular marker to further analyze the process of root cap cell separation and also provides a root cap specific promoter for targeting to the environment genes with beneficial properties for plant growth.

15 Claims, No Drawings

SEQUENCE LISTING

<160> NUMBER OF SEQ ID NOS: 12

<210> SEQ ID NO 1
<211> LENGTH: 1405
<212> TYPE: DNA
<213> ORGANISM: Arabidopsis Thaliana

<400> SEQUENCE: 1

```
gttccagaaa agaatcattg attactcgtt gtacataata tctccttcta aattgatgat      60
ttatagttat gtataacatg ttttgcaaga gatttgaaat cttcttatgt atcaattcaa     120
tgcttgtacc ctttttttat ccctcgagtt cttaaggtac ttagtcccta gtgattaacc     180
aaattagcca gcatatttct tttagaacat atatcatttt agaaaatatg ttactaaacg     240
atatgtttgg gcctttgatg atgaaaaagc taagaacgat tttcttttgg tatgaaatgt     300
ttgttattac tattcccttt agtatttacc aaagacttcg caggggggtga aaaaaaggat    360
caacctgatg ttatcatatt acacgtgaat ctcccagatc gagattttgc tacaagaatc     420
aagaaatatt atgtagggat tcgttgtgga acgagagaaa gtgtgttttg tttgcttaac     480
tttaaatctc agtttttctta taaacttttt atagccgtct tttatgcaaa accccttgag    540
ttttcatgc cttaacttgt gaatcgtgat agagtaagaa gattatggat attgttaagt      600
gttaattaag atcaatttca tcttctacga gatggtattc ctgtacgttt tccaatcaaa    660
taacttcatt ttaccattgt tattatttaa gaatatgtat atatataaga aagtgagttc    720
gatattttca tttgtatgta tataatgtaa aagattatac aataagacaa taataaagag    780
attaaggaat catttacgtg ttaatcacac ttgacttgag aaactctttt aaattgaagt    840
cctcctatag acccgtcgcc gttatcttgg cgccatttac gtaccctcct tttttctaaa    900
tcataatccc caaaatccct aacctaacta aactaaatac tacctaacta actaccctat    960
tatcaagatt taagacattg tttatctatc ccctaatcgt acgtattacg caatgccact   1020
atctaaaata cacttcatta cagtttactg tggtaaaaaa gataagtatc aaacatcaaa   1080
actaccaaga aattaccaat ttgtgtcggt gaactcatat agacaaacct atgtggtaat   1140
caaactatta gttaaaaaaa aattgaacat attaagaaga ttacagaata atacatgtaa   1200
tcctccactt gtcagttcta taaaatatta attaaaagg aaattcaaat tgaagtaact    1260
aagaacagtt ttttagcag ttaagctgaa tttcaaaaag ccataatctt cgctctgaat    1320
ctcatcagcc ccggtctcct tctctagcta tatatatacg tgtgtgataa agtcgtaccc   1380
tcaagccaac acaataacaa gaatg                                          1405
```

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2

```
gatgctgggg acaatgtgaa                                                  20
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
acggctcggc tcgggagaga ggaa                                   24

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4
aagatccttc caaattctcc atcctcgtca                             30

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
aagagccaaa gatgggcgtt tcta                                   24

<210> SEQ ID NO 6
<211> LENGTH: 37
<212> TYPE: DNA
<213> ORGANISM: Artificial Sequence
<220> FEATURE:
<223> OTHER INFORMATION: Synthetic

<400> SEQUENCE: 6
ggaaggacga ggagagggag atatagtgca ggcactg                     37

<210> SEQ ID NO 7
<211> LENGTH: 37
<212> TYPE: DNA
<213> ORGANISM: Artificial Sequence
<220> FEATURE:
<223> OTHER INFORMATION: Synthetic

<400> SEQUENCE: 7
ggatctagca aagtcacgta gcacacttgt cgaatag                     37

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
atggcagatg gtgaagacat tcag                                   24

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
gaagcacttc ctgtggacta ttga                                   24

<210> SEQ ID NO 10

```
<211> LENGTH: 24
<212> TYPE: DNA
<213> ORGANISM: Artificial Sequence
<220> FEATURE:
<223> OTHER INFORMATION: Synthetic

<400> SEQUENCE: 10
gattctcctt cttcctctac ccaa                                          24

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
gtaatgatga tggttagagt taaata                                        26

<210> SEQ ID NO 12
<211> LENGTH: 1455
<212> TYPE: DNA
<213> ORGANISM: Arabidopsis Thaliana

<400> SEQUENCE: 12
atggcttctc ctttcttctt tgtgttcctt ctctctgcgc tttcactgga gaataccta      60 gcaagtccca attacagaga agcactctca aagtcattac tcttttttcca aggtcagcgg    120 tctggtcgcc tccctagtga ccaacaactc tcatggaggt ctagctctgg cctctctgat    180
ggctcatctg ctcacgtgga cttgaccgga ggctactatg atgctgggga caatgtgaag    240 ttcaattttcc cgatggcgtt caccacaacc atgctttcct ggagctcttt ggagtacggt    300
aagaagatgg gacccgagct ccagaactcc cgtgtggcca tccgttgggc cacggattat    360
ctactgaaat gtgccagggc tacaccaggg aagctttacg ttggagtagg agatcctaat    420
ggtgaccaca agtgctggga acgaccagaa gatatgagca ctcctcgcac agtctactct    480
gtatctccct caaaccctgg ctctgatgta gccgctgaaa ccgctgctgc tctagctgca    540
agctccatgg tttttcaggaa agtagatccc aagtactctc gcttgctctt ggcgacagca    600
aagaaggtca tgcagtttgc cattcaatac cgaggcgctt acagtaattc cctttcctct    660
tccgtctgtc cgttctactg ctcctactct ggctacaagg acgagctact atggggagca    720
gcatggctac atagagcaac caacgacccg tattacacaa acttcataaa tccttagga    780 ggaggagatc agcctgacat cttcagttgg acaataaat acgccggtgc ctatgttctt    840
ctctcacgac gagcagtact aaacaaagac aacaactttg aactctacaa gcaagcagct    900
gagaatttca tgtgtaagat ccttccaaat tctccatcct cgtcaacaaa gtacactaaa    960
ggtggactga tgtacaaact acctcagagc aatctacaat acgtgacatc aataacattc   1020
ttgctcacca cctacgccaa atatatgaaa tccacaaaac aaactttcaa ctgcggaaac   1080
tcactaatcg tccccaacgc actgataaat ctatcgaagc gacaagtcga ttacgtcctc   1140
ggtgtgaatc caatgaagat gtcgtacatg gttggattca gctccaattt ccccaaaaga   1200
atccatcaca gaggttcctc tctcccgagc cgagccgtcc gttccaattc tctgggctgt   1260
aacggcggat tccaatcatt cagaacacaa aaccctaacc taacatatt aaccggagca   1320
```

-continued

```
attgtcggag gaccgaatca aaacgatgag tatccagacc agagagacga ttacacccga    1380
tcagagccag ctacatacat caacgccgca ttcgtcggac cattggcgta tttcgccgcc    1440
agccgatcgc cgtaa                                                     1455
```

ROOT CAP SPECIFIC PROMOTER AND METHODS OF USE IN PLANTS

GOVERNMENT SUPPORT

This invention was made with government support under Contract Number 2001-35304-10088 awarded by the United States Department of Agriculture and NSF-IPB 9817983. The government has certain rights in the invention.

BACKGROUND

One of the goals of plant genetic engineering is to produce a plant with desirable characteristics or traits. As such, plants have been generated where a native gene or an exogenous gene possessing a desirable characteristic is stably incorporated into the plant genome. Once incorporated, the native gene or exogenous gene is expressed. All cells of an organism contain more or less the same genetic information, yet genes are turned on and other turned off at different locations and times during the life cycle of the organism. An important component in gene expression is the promoter region. Promoters are the polynucleotide sequences upstream of a coding sequence that comprises the 5' regulatory elements controlling gene expression in living cells. There are many types of promoters which can be classified by the intended type of control of gene expression: constitutive, tissue-specific, inducible and synthetic. Inducible expression can be controlled chemically, such as chemicals not usually found in the plant, or physical, such as drought or light. Promoters can also be classified on the basis of regulation characteristics such as those temporally or developmentally regulated. Promoters can be used as tools to regulate expression of genes of interest. Isolated promoters that function in plants are useful for modifying plant phenotypes through methods of genetic engineering.

There is still a need for promoters capable of directing expression in a tissue specific manner, for example, a root cap cell specific manner.

This is also a need for a promoter useful to analyze the process of root cap cell sloughing and for targeting to the environment products with beneficial properties for plant growth.

There is also a need to modulate gene expression by chemical treatment of a transgenic plant having been transformed with a construct comprising a chemical sensitive promoter.

SUMMARY

The invention provides an AtCel5 gene promoter isolated from *Arabidopsis thaliana* that is expressed exclusively in root cap cells of both primary and secondary roots of any plant. The cDNA sequence of the AtCel 5 gene is found at GeneBank Accession number AY075630 and the coding region of the AtCel5 gene is as depicted in SEQ ID NO: 12. AtCel5 is believed to be a soluble and secreted protein that plays a role in the sloughing of root cap cells from the root tip. The sloughing of root cap cells from the root tip is important because it assists the growing root in penetrating the soil. The AtCel5 promoter provides a new molecular marker to further analyze the process of root cap cell separation and also provides a root cap specific promoter for targeting to the environment genes with beneficial properties for plant growth.

In accordance with the invention, a promoter comprising an isolated or recombinant polynucleotide sequence substantially homologous to a polynucleotide sequence of the promoter region (SEQ ID NO: 1) of AtCel5, or a fragment thereof having promoter activity, particularly in the root cap cells of a plant. The AtCel5 promoter was isolated by the inventors from *Arabidopsis thaliana* and is useful for the expression of transgenes of importance in the study of root development and the modification of the rhizosphere surrounding the roots of a transgenic plant. This promoter is of particular benefit for directing transgene expression in root cap cells.

Also claimed is a construct comprising the above promoter operably linked to a transcribable polynucleotide molecule, for example, a marker gene such as, but not limited to, the GUS gene. The construct is also useful to transform a plant to express proteins such as but not limited to antifungals, antibacterials, antiparasitics, antivirals anti nematodes and growth factors. As such, the plant can be protected from infection, induced to grow roots or altered in any desirable manner. The construct can also be employed to confer attributes such as but not limited to modulated nutrient uptake, modulated toxin uptake, modulated water uptake, modulated sugar production, modulated starch production, modulated oil production and the like. In one embodiment, the construct comprises a transcribable polynucleotide molecule which encodes an endo-1,4-beta-D-glucanase.

Also described is a transgenic plant stably transformed with the above construct. The plant may be a crop, such as a root crop, selected from the group consisting of, but not limited to, *Arabidopsis*, tomato, tobacco, potato, corn, beets, carrots and most dicot plants. The transgenic plant being transformed with a construct of the invention may possess altered cell proliferation in mature root cap cells, in particular, root caps cells that begin expression of the construct at least about 30 hours post-germination and which continue expression for at least about 3 weeks. Another alteration conferred to a transgenic plant of the invention is altered root cap cell sloughing to a transgenic plant.

Further disclosed is a seed or a part of a transgenic plant transformed with a construct of the invention. In one embodiment, the part is a cell, for example a root cap cell.

The invention also relates to an expression vector comprising the promoter or an expression vector comprising a construct which comprises the promoter. In one embodiment, the expression vector is the pBI101 plant transformation vector. A host transformed with the expression vector of the invention is also disclosed. In one embodiment, the host cell is *Agrobacterium* gv3101.

Methods of using the compositions of the invention are also disclosed. In one embodiment, a method of directing expression of a gene to root cap cells comprising expressing a chimeric gene construct where a gene of interest is fused to a promoter of the invention. Another method described is a method for destroying soil pathogens comprising expressing in a plant a chimeric gene construct comprising a root cap-specific promoter fused upstream of genes expressing proteins that destroy soil pathogens.

Applicants have also disclosed a method for reducing heavy metals in soil comprising expressing in a plant a chimeric gene construct comprising a root cap-specific promoter fused upstream of a gene expressing a heavy metal binding protein. In one embodiment, the gene expressing the heavy metal binding protein is endogenous to the root cap. Also described is a method for enhancing root penetration into soil comprising expressing in a plant a construct comprising the promoter of the invention operably linked to a transcribable polynucleotide molecule. In one particular embodiment, the promoter is the AtCel5 promoter.

Applicants also disclose the sensitivity of the promoter to chemicals. In one embodiment, a method of decreasing the expression of the promoter of the invention in a transgenic plant by administering said transgenic plant with auxin (IAA), 1 aminocyclo-propane-1 carboxylic acid (ACC) or exogenous abscissic acid (ABA).

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end. As used herein, the term "polynucleotide sequence" refers to the sequence of a polynucleotide molecule.

As used herein, the term "promoter" refers to a polynucleotide molecule that, in its native state, is located upstream or 5' to a translational start codon of an open reading frame (or protein-coding region) and that is involved in recognition and binding of RNA polymerase II and other proteins (trans-acting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated with. Plant promoters can include promoters produced through the manipulation of known promoters to produce artificial, chimeric, or hybrid promoters. Thus, the design, construction, and use of chimeric or hybrid promoters comprising a polynucleotide sequence substantially homologous to SEQ ID NO: 1 or a fragment thereof having promoter activity for modulating the expression of operably linked polynucleotide sequences is encompassed by the present invention.

As used herein, the term "substantially homologous" refers to polynucleotide molecules that demonstrate a substantial percent sequence identity with the promoters provided herein, wherein the polynucleotide molecules function in plants to direct transcription and have at least about 70% sequence identity, at least about 80% sequence identity, at least about 85% sequence identity, at least about 90% sequence identity, or even greater sequence identity, such as 98% or 99% sequence identity with the polynucleotide sequences of the promoters described herein. Polynucleotide molecules that are capable of regulating transcription of operably linked transcribable polynucleotide molecules particularly in a root cap cell of a plant, and that are substantially homologous to the polynucleotide sequences of the promoters provided herein are encompassed within the scope of this invention. In one preferred embodiment, polynucleotide molecules of the invention having promoter activity, particularly in a root cap cell of a plant, have at least about 85% sequence identity with the polynucleotide sequence of SEQ ID NO: 1.

As used herein, the term "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG.RTM. Wisconsin Package.RTM. (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology.

The term "stringent conditions" is functionally defined with regard to the hybridization of a nucleic-acid probe to a target nucleic acid (i.e., to a particular nucleic-acid sequence of interest) by the specific hybridization procedure discussed in Molecular Cloning: A Laboratory Manual, $3^{rd}$ edition Volumes 1, 2, and 3. J. F. Sambrook, D. W. Russell, and N. Irwin, Cold Spring Harbor Laboratory Press, 2000 (referred to herein as Sambrook, et al.). Accordingly, the nucleotide sequences of the invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence.

For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2×SSC, 0.1% SDS, 65° C.). Appropriate moderate stringency conditions that promote DNA hybridization, for example, 6.0× sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2×SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art. Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues".

In another embodiment, the promoter disclosed herein can be modified. Those skilled in the art can create promoters that have variations in the polynucleotide sequence. The polynucleotide sequences of the promoter of the present invention may be modified or altered to enhance its control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. A "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. For example, promoters can be constructed such that promoter fragments or elements are operably linked, for example, by placing such a fragment upstream of a minimal promoter. The elements and fragments of the promoter of the present invention can be used for the construction of such chimeric promoters. Methods for construction of chimeric and variant promoters of the present invention include, but are not limited to, combining control elements of different promoters or duplicating portions or regions of a promoter. Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NO: 1 or a substantially homologous polynucleotide sequence having promoter activity, includes any length of said polynucleotide sequence that has promoter activity, e.g., is capable of regulating transcription of an operably linked transcribable polynucleotide molecule. For example, the promoter as disclosed in SEQ ID NO: 1 may be truncated or portions deleted and still be capable of regulating transcription of an operably linked polynucleotide molecule. In particular embodiments, promoter fragments may be provided comprising at least about 30, 50, 70, 90, 110, 125, 150 or about 200 or longer nucleotides. In specific embodiments, these fragments may comprise contiguous portions of the sequences disclosed in SEQ ID NO: 1.

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art; see for example, Sambrook, et al.

Constructs of the present invention would typically contain a promoter of the invention operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. These additional upstream and downstream regulatory polynucleotide molecules may be derived from a source that is native or heterologous with respect to the other elements present on the promoter construct.

Thus, constructs of the present invention comprise a promoter of the invention such as that provided in SEQ ID NO: 1 or modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

A promoter of the present invention can be incorporated into a construct using marker genes as described and tested in transient analyses that provide an indication of gene expression in stable plant systems. As used herein the term "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art.

In one preferred embodiment, a promoter of the present invention is operably linked to a transcribable polynucleotide molecule that is a gene of interest including but not limited to a gene that provides a desirable characteristic associated with plant morphology, physiology, growth and development, yield, nutritional enhancement, disease or pest resistance, or environmental or chemical tolerance. Alternatively, a transcribable polynucleotide molecule can effect the above mentioned phenotypes by encoding a non-translatable RNA molecule that causes the targeted inhibition of expression of an endogenous gene, for example via antisense, RNAi, or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest is useful for the practice of the present invention.

As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation, microprojectile bombardment and protoplast transformation. The transformed plants are generally analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The seeds of this invention can be harvested from fertile transgenic plants and be used to grow progeny generations of transformed plants of this invention including hybrid plant lines comprising the construct of this invention and expressing a gene of interest.

Endo-1,4-β-D-glucanases (EC 3.2.1.4) are a wide-spread group of enzymes that hydrolyze the β-1,4-glucosidic bond between two glucose moieties. These genes are thought to be important to basic plant development and are also referred to as cellulases. In *Arabidopsis*, the endo-1,4-β-D-glucanase family is composed of 25 members, of which approximately half are attributable to tandem duplication of genes and duplication of genome DNA segments. This relatively large family is comprised of many proteins with a putative signal peptide at the amino terminus (predicted to be secreted) and a few proteins with a membrane spanning domain (predicted to be non-secreted) (del Campillo, 1999). Both secreted and non-secreted forms share the same catalytic amino acid signature toward the carboxy terminal end. This signature places all 25 genes into the Glycosyl Hydrolase family 9 (GH9), formerly known as cellulase family E (Henrissat, 1991; Henrissat and Bairoch, 1993; 1996). Thus, while the protein function of all members of this family is known (endo-1,4-β-D-glucanases), for most members, the role they play in plant development is unknown. In many plants, the secreted endo-1,4-β-D-glucanases (cellulases) have been correlated with processes that require progressive disassembly and breakdown of the cell wall, including fruit ripening, (Lashbrook et al., 1994), anther dehiscence (del Campillo and Lewis, 1992), vascular tissue differentiation (Milioni et al., 2001, 2002) and abscission of plant organs, (Tucker et al., 1988; del Campillo and Bennett, 1996; Gonzalez-Bosch et al., 1997).

Applicants studied At1g22880, an *Arabidopsis* endo-1,4-β-D-glucanase that is predicted to be soluble and secreted. Applicants initially isolated this gene as a genomic clone that cross-hybridized with the tomato abscission cellulose Cel5 (del Campillo and Bennett, 1996; Kalaitzis et al., 1999), and thereby it was designated AtCel5. Applicants analyzed the spatial and temporal expression of AtCel5 using a promoter-GUS reporter approach and RT-PCR. Although Applicants initially speculated that this gene would play a role in *Arabidopsis* flower abscission, Applicants show here that it is expressed exclusively in root cap cells. AtCel5-GUS expression is distinct from other known promoter-reporter constructs that are specific to the root tip and thus provides a new molecular tool for studying root cap development and root cap cell-cell separation.

The sloughing of root cap cells from the root tip is important because it assists the growing root in penetrating the soil. Using a ATcel5 promoter-reporter (GUS) and RT-PCR analysis, Applicants identified an endo-β-1,4-glucanase (AtCel5) of *Arabidopsis thaliana* that is expressed exclusively in root cap cells of both primary and secondary roots. Expression is inhibited by high concentrations of IAA, both exogenous and internal, as well as by ABA AtCel5 expression begins once the mature tissue pattern is established and continues for 3 weeks. GUS staining is observed in both root cap cells that are still attached and cells that have already been shed. Using AtCel5-GUS as a marker, Applicants observed that the root cap cells begin to separate at the sides of the tip while the cells of the central region of the tip separate last. Separation involves sequential tiers of intact cells that separate from the periphery of the root tip. A homozygous T-DNA insertion mutant that does not express AtCel5 forms the root cap and sheds root cap cells but sloughing is less efficient compared to wild type. The reduction in sloughing in the mutant does not affect the overall growth performance of the plant in loose media. The modest effect of abolishing AtCel5 expression suggests that there are multiple redundant genes regulating the process of sloughing of the root cap, including AtCel3/At1g71380, the paralog of the AtCel5 gene that is also expressed in the root cap cells. Thus, these two endo-1,4-β-D-glucanases may have a role in the sloughing of border cells from the root tip. As such, AtCel5 provides a new molecular marker to further analyze the process of root cap cell separation and a root cap specific promoter for targeting to the environment genes with beneficial properties for plant growth.

Thus, the invention relates to altering root cap cells to enhance plant growth, enhance the soil in which the plant grows or both. In one aspect, the altered root cap cell results in altered exudates being sloughed off into the environment, in particular, the rhizosphere. Microorganisms compete in the rhizosphere, an area rich in exudates from the plant. The exudates contain carbohydrates, organic acids, vitamins and many other substances essential for life. For example, in one embodiment, from about 5 percent to about 40 percent of the total dry matter production of organic carbon from photosynthesis may be released as exudates into the rhizosphere. When plants begin to decline, the amount of organic carbon released as exudates increases. Mineral deficiencies, low amounts of soil air and severe wounding are major causes for the increase in exudates. The compositions and methods of the invention are suitable for altering the amount and composition of the exudates.

In the practice of the invention, the Applicants identified a homozygous, T-DNA knockout of At1g22880, cel5, from the Salk collection, (Alonso et al., 2003) and Applicants show that this mutant does not express AtCel5. Morphological characterization of wild type and mutant cel5 failed to display distinct phenotypic differences at the whole plant level. However, a close examination of the root tip revealed that the mutant displays an increase in the retention of the root cap compared to wild type in response to friction and handling. Analysis of the duplicated segments of chromosome 1 of *Arabidopsis* revealed that the AtCel5 gene is positioned in a segment of the upper arm, which is duplicated in the lower arm. The AtCel5 duplicon (AtCel3/At1g71380) shares not only 81.9% sequence identity over the coding region but also the identity extends to the non-coding promoter region as well. Therefore, in addition to the characterization of AtCel5, Applicants analyzed the expression of the AtCel3. Applicants conclude that these two genes have redundant functions.

Of particular interest in the practice of the invention is the family 9 of glycosyl hydrolases (endo-1,4-β-D-glucanases) which constitute a group of enzymes that can hydrolyze internal linkages in 1,4-β-glucan substrates. The most conspicuous β-1,4 glucan present in plants is cellulose, which is the most important structural component of the cell wall. In addition, other more complex glucan polymers bearing β-1,4 linkages are also found in the cell wall. These polymers are secreted outside the plasma membrane and organized into a complex cell wall matrix. Most plants contain in their genome multiple sequences coding for the family 9 glycosyl hydrolases (GH9). In *Arabidopsis*, this family consists of 25 members and comprises a few membrane proteins that could be anchored at the plasma membrane and a large number of proteins with a predicted amino acid signal in the N terminus that would direct secretion to the cell wall. Although the specific glucans that this family acts on in the plant cell wall are not known, it is generally believed that the secreted members are important in processes that entail cell wall disassembly.

Applicants analyzed the expression of one member of the *Arabidopsis* GH9 family. This putative hydrolase, predicted to be soluble and secreted, was initially isolated from an *Arabidopsis* genomic library that was probed with the tomato cellulase, Cel5. Since the tomato Cel5 gene is expressed in tomato flower abscission (del Campillo and Bennett, 1996; Kalaitzis et al., 1999), Applicants initially expected the *Arabidopsis* AtCel5 gene to be expressed in *Arabidopsis* flower abscission. What Applicants discovered was quite different and surprising. There was no AtCel5 expression in abscission zones or any other aerial tissue of mature plants. Instead, expression was strong and exclusive to the root cap cells. Consistent with these results, a search of EST databases revealed expression of this gene only in root cDNA libraries. Moreover, Applicants' analysis of the Cel5 promoter region indicated the presence of cis-motifs common to root specific genes. AtCel5 expression starts at the very tip of the root cap cells approximately 30-48 hours post-germination and continues for at least 3 weeks. Expression was not linked to growth processes such as the emergence of roots from seeds, the initiation of lateral roots or root hairs, or the elongation of roots.

Root cap cells are ultimately shed from the plant tips and GUS activity was detected not only in the root cap cells that were still attached to the root, but also in cells that had already been shed. Thus, this transgenic *Arabidopsis*, with GUS expression exclusively in the root cap cells, provides a novel molecular marker to further analyze the process of root cap cell separation. A xylogalacturonan (XGA) epitope that is specific to detaching cells (Willats et al., 2004) has already been identified in several plant species. The use of these markers will stimulate research to specifically address root cap cell separation in *Arabidopsis*.

The sloughing of root tips is primarily a process of cell-cell separation that results in the shedding of living cells with modified cell walls. These cells then degenerate to contribute the mucilaginous material around the root tip (Hawes, 1990). The whole process is likely to require an ensemble of hydrolytic enzymes. Recent evidence indicates that in pea roots (Wen et al., 1999), a pectin methyl esterase gene is important for root cap cell separation. The results from this work suggest that AtCel5 is also involved in this process, either during cell-cell separation or cell-wall breakdown after shedding to provide polysaccharide precursors for mucilage production or both.

Applicants' microscopic observations revealed that in *Arabidopsis*, the root cap cells begin to separate at the sides of the tip while the cells of the central region of the tip separate last. Separation involves sequential tiers of intact cells that separate from the periphery of the root tip. Since AtCel5 begins to accumulate in the central region of the root tip, this would suggest that the root cap separation process involves more than the expression of AtCel5. Nonetheless, an additional factor to consider is that as the root meristem develops and the root extends and expands, the shearing forces experienced by the peripheral cells might be greater than the cells positioned directly at the tip. These forces may thereby accelerate separation in the peripheral cells.

Applicants' description is consistent with observations of bean root border cells that also separate as intact, metabolically active root cells, and eventually degenerate to contribute the mucilaginous material at the root tip (Hawes, 1990; Hawes et al., 1998; Miyasaka and Hawes, 2001). To Applicants' knowledge, this is one of the first detailed descriptions of the root cap separation process in *Arabidopsis*. Root cap sloughing has been linked to the ability of the root to penetrate through the soil (Bengough and Mckenzie, 1997; Iijima et al., 2003). Consistent with this, Applicants detected more stained root cap cells in the process of separation from the root tip on plates containing 4% agar that imposed more physical impediment as well as osmotic stress. Although this observation suggests there was more root cap separation, RT-PCR did not detect an increase in the AtCel5 transcript levels as the percent agar increased in the medium. It is possible that the RT-PCR was not sensitive enough to detect these differences. An alternative interpretation could be that the increase in stained root cap cells was the result of greater retention or appression of the root cap cells around the root tip periphery. Applicants also found that high auxin and ABA concentration both negatively regulate AtCel5 expression. High exogenous or internal auxin had an inhibitory effect on root elongation and ultimately arrested root growth. Similarly, the addition of ABA, which mimics some aspects of the water stress responses, inhibited AtCel5-GUS expression. Moreover, sequence analysis of the AtCel5 promoter region identified several cis-acting elements involved in regulating gene expression in response to ABA, drought and dehydration. These experiments showed that when root elongation stopped, AtCel5-GUS expression ceased, as was also observed in seedlings growing in high external ACC concentration or etiolated seedlings kept for 1 week in the dark. These observations suggest that AtCel5 is associated with active root cap growth, more specifically, with processes such as the initial loosening and ultimate sloughing of cells of the root cap.

In addition to the above, Applicants identified a homozygous cel5 knockout mutant plant and confirmed by RT-PCR that the AtCel5 mRNA was not expressed. Although the cel5 mutant appeared phenotypically the same as wild type under normal growth conditions, a more detailed comparison of root cap tissue indicated that there is more root cap sloughing in the wild type compared to cel5 mutant. The reduction in sloughing in the mutant apparently did not affect the overall growth performance of the plant in loose media. This would account for the lack of obvious phenotypic differences. The modest effect of abolishing AtCel5 expression suggests that there are multiple redundant genes regulating the process of sloughing of the root cap, or that overall growth performance is only significantly affected by the rate of sloughing for plants cultivated on compacted soil (cf. Iijima et al., 2003). With regard to the former, Applicants identified in the *Arabidopsis* genome a duplicon of AtCel5, which is referred to as AtCel3/At1g71380. A cDNA for this paralog was initially isolated from *Arabidopsis* cells growing in suspension cultures and referred to as a β-glucanase (Lu and Ferl, 1995). A proteomic analysis of cell wall proteins in *Arabidopsis* confirmed that this gene is abundantly expressed in cell suspension cultures (Borderies et al., 2003). A recent conference report described expression of AtCel3 in abscission zones of *Arabidopsis* flowers (Thoma et al., 2003) and thus its role in the root could be overlapping with AtCel5, while distinct in abscission zones.

The AtCel3 and AtCel5 genes have the same number of amino acids (484 aa), same gene organization (five exons and four introns in the same relative position), and share a 89.1% amino acid identity. At the nucleotide level, both coding sequences (CDSs) have 81.9% identity and the whole unspliced sequence shares 75.5% identity. Moreover, the sequence identity between AtCel5 and AtCel3 extends 1000 bp upstream from the ATG. Consistent with such promoter similarities, Applicants found that the AtCel5 duplicon is also expressed in roots. In a recent work that mapped the expression of genes in distinct root cell types in *Arabidopsis* by microarray (Birnbaum et al., 2003), both genes were shown to be expressed in the epidermal cells of the root cap region (LED 5, stage 1). Consistent also with Applicants' data, Birnbaum et al., demonstrated that the expression of both genes drops precipitously in stages 2 and 3 (Birnbaum et al., 2003 supplemental material). Therefore, it is believed that both genes AtCel5 and AtCel3 are expressed in root cap cells and both are involved in root cap sloughing.

In addition, the significant levels of CM-cellulase activity that was detected in the media in which *Arabidopsis* seedlings were growing is attributed to AtCel5 and AtCel3 activity in the root cap. Applicants' data support the model that *Arabidopsis* root elongation and root cap cell separation are concomitant processes and that separation requires AtCel5 and AtCel3 expression. In order to establish the role of each gene in root cap separation, it will be necessary to inhibit both AtCel5 and AtCel3 and these efforts are currently underway.

Applicants believe that more detailed analyses may demonstrate that the plant's ability to shed cells at the root cap is necessary to survive certain environmental conditions. The function of shedding the root cap is unknown; however, it has been suggested that the root cap could provide a selective advantage to the plant by releasing specific chemicals that regulate root-associated microorganisms (Hawes, 1990; Hawes et al., 1998). Studies of root cap development are aided by using AtCel5-GUS expression as a specific marker of root cap cells. In addition, the root cap specificity of the AtCel5 promoter provides a new tool for targeting to the environment genes with beneficial properties for plant growth.

By way of illustration, the Applicants offer the following non-limiting examples. In reviewing the non-limiting examples, those of skill in the art will be able to discern the broader applicability of the invention as further described in this application in its entirety.

EXEMPLIFICATION

Example 1

Plant Material and Growth Conditions

*Arabidopsis* ecotype Columbia was used in all the Examples described here. Seeds were surface-sterilized using 0.3% sodium hypochlorite for 5 minutes, rinsed in sterile water five times and plated on medium consisting of half-strength MS (Murashige and Skoog, 1962) basal salts (Sigma), 0.5 g/l 2-[N-Morpholino]ethanesulfonic acid (Sigma, St. Louis, Mo., USA), pH 5.7, supplemented with 1·Gamborg's vitamins and solidified with 1% (w/v) plant tissue culture agar (Type E, Sigma). Additional filter-sterilized stock chemicals (1000×) were added to the warm agar mixture after autoclaving. Plated seeds were cold treated for 4 days at 4° C. and then plates were placed vertically in a growth chamber at constant 20° C. under 16-h light/8-h-dark regime. For the root cap retention assay, plates were sliced in the middle and one half of the agar media was removed. Seeds were plated on the ledge of the agar so that the roots were forced to grow vertically through the agar. For germination in dark conditions, plates were set in the same incubator and covered with two layers of aluminum foil. Seeds were also planted and grown to maturity on soil (Metro-Mix 300, Scotts Company) in a growth chamber at 20° C. under 16-hour light/8-hour-dark cycle.

Example 2

Hormone Experiments

To investigate the influence of indole-3-acetic acid (IAA; Sigma) plants were grown under liquid conditions as well as vertical plates. In all experiments the roots were separated from the shoots, frozen in liquid Nitrogen, and stored at −80° C. prior to analysis. Seedlings expressing a promoter-reporter (AtCel5-GUS) were grown for 2 weeks in flasks containing 50 ml of half-strength MS media supplemented with 50 µM IAA (50 µl of a 50 mM solution in DMSO), with control consisting of the same volume of liquid media containing a comparable amount of DMSO. Seeds were cold treated for 4 days at 4° C. to promote even germination. Liquid cultures were placed on a rotary shaker at 120 rpm and grown under 24 hours of fluorescent light at room temperature. To determine the effects of auxin, and the IAA transport inhibitor, N-1-naphthylphthalamic acid (NPA; Pfaltz and Bauer, Inc.), seeds expressing AtCel5-GUS were grown in half-strength MS media solidified with agar and supplemented either with, 10 µM IAA, 1 µM NPA or a comparable amount of DMSO solvent (control). Plates were transferred to the light incubator for 10 days and set in a vertical position. The inhibitory effect of NPA on root gravity perception was examined by observing the direction of root growth in plates set in a horizontal position.

For analysis of ethylene regulation, seeds expressing AtCel5-GUS were plated on agar containing half-strength MS medium supplemented with 10 µM of 1 aminocyclopropane-1 carboxylic acid (ACC; Sigma), made from a stock (1000×) prepared in water. After cold treatment for 4 days at 4° C., plates were transferred to the light incubator for 7 days and set in a vertical position.

For analysis of the effects of ABA, a 100 mM ABA stock solution was prepared in 100% ethanol (13.22 mg ABA/0.5 ml) and then diluted 1000× in water. Seeds expressing AtCel5-GUS were plated on agar basal medium and grown for 7 and 10 days. Under sterile conditions, plates with seedlings were opened and 10 ml of 100 µM ABA was added to bathe the seedlings. Plates were then set horizontally in the light incubator for 24 hours.

Example 3

Promoter-Reporter Construction

To characterize the AtCel5 promoter, a chimeric construct was generated by fusing a fragment of the putative promoter in frame with the GUS gene. The promoter was derived from an *Arabidopsis* 5 kb genomic clone that contained the gene. One such suitable clone is the BAC clone F19G10. The clone was first restricted with XbaI/NcoI to generate a 3.2 kb fragment, containing the promoter plus the first exon of the AtCel5 gene. The 3.2 kb fragment was then restricted with XmnI in order to separate the first exon from the promoter. The fragment flanked by XmnI restriction sites that contained 1400-bp of the putative promoter plus the 5' UTR and the ATG translation start of ATCel5 was cloned upstream of the GUS gene in the pBI101 plant transformation vector that was opened at the SmaI site. A plasmid containing the promoter fragment in the sense orientation with respect to the GUS gene was selected based on endonuclease restriction digestion and confirmed by DNA sequence. The construct also contains the NPTII gene which confers kanamycin resistance and was delivered to wild-type plants via *Agrobacterium* transformation by the floral dip method (Bent, 2000). Seeds derived from transformed plants were selected in germination media containing kanamycin.

Example 4

SEM Microscopy

Two to 14 day-old seedlings were collected on ice and fixed in 4% (w/v) glutaraldehyde in 50 mM potassium phosphate buffer, pH 7.2 under vacuum overnight at 4° C. After fixation, tissues were rinsed with buffer, dehydrated in an ethanol series, and dried in a critical point dryer in liquid carbon dioxide at the SEM facility (University of Wisconsin, Madison, Wis., USA). Tissues were then mounted on scanning electron microscope stubs, coated with gold palladium, and examined using a scanning electron microscope (Hitachi S-570; Hitachi Ltd., Tokyo, Japan) at an accelerating voltage of 10 kV. Fifteen to 20 samples of each plant line were photographed using Gatan Digital capture system.

Example 5

Histochemical GUS Analysis

Plant tissues were collected in 90% acetone and incubated on ice for at least 10 min. Tissues were rinsed with 50 mM NaPO$_4$ pH 7.2, 0.5 mM K$_4$Fe(CN)$_6$ and 0.5 mM K$_4$Fe(CN)$_6$ and then placed in staining solution (2 mM 5-bromo-4-chloro-3-indolyl-β-D-glucopyranoside [X-Glu; Sigma] in rinse solution), vacuum infiltrated for 10 minutes and finally incubated at 37° C. for 2 hours or overnight. Seedlings were examined using a microscope and photographed with a Digital Nikon 990 Camera.

Example 6

Fluorometric GUS Analysis

Quantification of GUS activity was performed according to the method of Jefferson et al. (1987) using the fluorogenic substrate MUG (4-methyl-umbelliferyl-β-D-glucuronide). Only root tissue was used to analyze GUS activity. Tissues were ground in MUG extraction buffer and centrifuged for 5 minutes, at maximal speed in a microfuge, to clear the supernatant. An aliquot of crude extract containing the same number of root tips per treatment was mixed with the MUG reaction buffer containing 2 mM MUG and incubated at 37° C. Five or six aliquots were taken from the enzyme reaction at 60 minute intervals. At each time point, the reaction was stopped with 0.2 M Na$_2$CO$_3$. Fluorescence was determined using a one-channel fluorometer (Turner Designs Picofluor) with an excitation range of 365-395 nm and emission wavelengths of greater than 430 nm. The fitted linear slope (±standard error) of fluorescence vs. incubation time was used as a relative measure of GUS content for comparison of controls and treatments.

Example 7

RNA Isolation and RT-PCR Analysis

For tissue specificity studies, total RNA was isolated from 200 mg of different plant tissues (buds, green siliques, rosette leaves, stems and roots) as described in the RNeasy Plant Mini Kit (Qiagen, Chatsworth, Calif.). For each sample, a one step RT-PCR (Qiagen kit) was performed with 1 µg of total RNA for a total of 35 cycles following the recommendations of the manufacture. The primers (AtCel5 set I) used for these PCR reactions, Fw-5'-GATGCTG-GGGACAATGTGAA-3' (SEQ ID NO: 2), Rv-5'-ACGGCTCGGCTCGG-GAGAGAGGAA-3' (SEQ ID NO: 3), were derived from the first exon and last exon, respectively. Thus, there was an approximate 400 bp size difference between the PCR product derived from the reverse transcribed mRNA and that derived from traces of genomic DNA present in the sample. Products were run on 1% agarose gels. PCR cycles included 1 min denaturation at 94° C., followed by 1 minute annealing at 48° C. and a final 2 minute extension at 72° C.

For comparative RT-PCR analysis of roots exposed to various treatments, or the analysis of expression of the AtCel5 duplicon, a two-step RT-PCR was performed using the Retroscript kit (Ambion, Austin, Tex.). Total root RNA was pretreated with DNAse prior to reverse transcription (Ambion DNA-free kit). The first strand cDNA was prepared with oligo dT primers and used as template for PCR reactions. RT-PCR was normalized using Actin-11 or KOR as internal standards. The primers used were:

```
for AtCel5 (set II),
                                     (SEQ ID NO: 4)
Fw-5'-AAGATCCTTCCAAATTCTCCATCCTCGTCA-3', (SEQ ID NO: 5)
Rv-5'AAGAGCCAAAGATGGGCGTTTCTA-3';

for KOR,
                                     (SEQ ID NO: 6)
Fw-5' GGAAGGACGAGGAGAGGGAGATATAGTGCAGGCACTG-3', (SEQ ID NO: 7)
Rv-5' GGATCTAGCAAAGTCACGTAGCACACT-TGTCGAATAG-3';

For Actin-11,
                                     (SEQ ID NO: 8)
Fw-5'-ATGGCAGATGGTGAAGACATTCAG-3';

(SEQ ID NO: 9)
Rv-5'-GAAGCACTTCCTGTGGACTATT GA-3'.

For AtCel3, primers were
                                     (SEQ ID NO: 10)
Fw-5'-GATTCTCCTTCTT-CCTCTACCCAA-3', (SEQ ID NO: 11)
Rv-5'-GTAATGATGATGGTTAGAGTTAAATA-3'.
```

Each PCR reaction was run for 25 cycles. Each cycle included a denaturation and an extension step at 94° C. for 45 seconds, and at 72° C. for 70 seconds, respectively. The annealing step was carried out for 30 seconds at the temperature optimal for each primer pair:

AtCel5 (set II), 58° C.; KOR, 62° C.; Actin-11, 60° C.; AtCel3, 65° C.

Example 8

Root Length Measurements

Approximately 20 seedlings were grown on vertical plates for 10 days in conditions as previously described. Seedlings and a ruler held adjacent to the seedlings were digitally photographed. Root length calculations were performed on the digital images using the NIH ImageJ software.

Example 9

Cloning and Basic ATCel5 Information

Applicants initially isolated a lambda clone containing the AtCel5 gene from an *Arabidopsis* genomic library that was probed with the tomato cellulase, Cel5. The tomato Cel5 gene is expressed in tomato flower abscission (del Campillo and Bennett, 1996; Kalaitzis et al., 1999). When the *Arabidopsis* clone was partially sequenced, Applicants found that it matched a putative endo-1,4-β-D-glucanase gene in the BAC clone F19G10. The predicted amino acid sequence of the AtCel5 gene is 484 amino acids (aa) long, with a molecular weight 54 kDa, pI 9.53 (GenBank Accession number AY075630, MIPS At1g22880; BAC F19G10.16). The gene is located on the upper arm of chromosome 1, positions 8,095, 768 to 8,097,537 bp. The open reading frame of AtCel5 is composed of five exons interrupted by four short introns. The protein has a predicted 22 aa signal peptide indicating that the nascent polypeptide is imported into the endoplasmic reticulum and then secreted outside the cell. In addition, this protein appears not to be glycosylated as indicated by the absence of predicted ASN N-glycosylation sites (PS00001).

Applicants also analyzed the 5' flanking region upstream from the translation start site. This segment is 1400 nucleotides long, AT-rich (69% A+T; 31% C+G) and contains the motif TAACAA/GA and the CAAT boxes common to many actively transcribed plant genes. Based on the Plant cis-acting regulatory DNA elements (PLACE) signal database (Higo et al., 1999), the root motif ATATT (S000098) is repeated 13 times through the 1400 bp sequence. Moreover, in the 5' upstream sequence there are two consensus sequences, GAGAGA and GAAAAAG, which have been found in genes up-regulated 30 minutes after gravistimulation (Moseyko et al., 2002) and two TACGTG elements that relate to drought and ABA response (Iwasaki et al., 1995). Applicants also found the cis-acting regulatory elements CAGGTG and CACTTGT, which have been described as binding sites for basic helix-loop-helix transcription factors that regulate gene expression in drought and ABA responsiveness in *Arabidopsis* (Jaglo-Ottosen et al., 1998).

Example 10

Tissue Specificity and Developmental Regulation

Although the tomato Cel5 gene is expressed in floral abscission zones, Applicants found no expression of AtCel5 in aerial plant tissues of *Arabidopsis* by northern blot analysis (data not shown). A search of EST databases revealed expression of this gene in a root cDNA library (GenBank Accession number AV540005). The specificity of gene expression to the root was confirmed by RT-PCR analysis (not shown. Only root RNA showed a PCR product of the expected size and the sequence of AtCel5 cDNA.

Example 11

To further analyze tissue and cell specific expression of AtCel5, a promoter-reporter fusion (AtCel5-GUS) was prepared between an upstream DNA segment (1400 bp) of the AtCel5 gene and the *E. coli* b-glucuronidase (GUS) gene (Jefferson, 1987). The putative promoter fragment included also the 5' UTR and the ATG translation start of the AtCel5 gene. Five independent lines resistant to kanamycin were selected and all displayed root-specific GUS expression. The expression was localized to the primary root apex and to the lateral root tips of young seedlings grown on agar plates. Staining was seen throughout the outermost layer of the root tip. GUS activity was also observed in root tips of plants grown in soil (data not shown).

To determine the onset of AtCel5 expression during seedling development, GUS staining was monitored daily on seedlings growing in agar plates. There was no detectable AtCel5-GUS expression during the initial emergence of the primary root suggesting that this gene is not linked to seed germination. Applicants determined that AtCel5-GUS expression begins in the primary root tip around 30-48 hours post-germination and continues for at least three weeks.

Similarly, in lateral roots, AtCel5-GUS expression was not detected at emergence and only began once the roots were approximately 2 mm in length, after the mature tissue pattern was established (Laskowski et al., 1995). Expression was initially localized to the cells in the center of the outermost layer of the root tip. It is important to note that staining was not detected at initiation or elongation of root hairs (data not shown).

Example 12

Expression Patterns

The expression of AtCel5-GUS is specific to the root cap, in contrast with the expression of other genes that are specifically expressed in the root tip, such as DR-5 (Ulmasov et al., 1997) and mitotic cyclin CYCB1 (DiDonato et al., 2004). By comparison, DR-5 is expressed throughout the root tip, whereas mitotic cyclin B1 expression is specific to the meristematic cells positioned behind the root cap. When the GUS assay was performed on seedlings growing on agar plates without removing the roots from the media, stained material was detected on the surface of the agar. A microscopic examination of this material shows to be cells shed from the root cap. When seedlings were grown in the dark, at 20° C., AtCel5-GUS expression was detected in the root tip approximately 48 hours post-germination, but was not present after 1 week. In the dark, root elongation is inhibited and Applicants detected no change in root length between days 2 and 7. Nevertheless, when the etiolated seedlings were returned to the light, the seedlings started to green, elongation of the roots resumed and AtCel5-GUS expression at the root tips was restored (data not shown). Lastly, GUS staining was not detected in any aerial tissue of seedlings or mature flowering plants (data not shown). These data suggest that AtCel5 is expressed exclusively in root cap cells, that expression is active as long as the root tips are growing and that AtCel5 appears to be associated with the process of root cap separation, usually referred to as sloughing. The sloughing of root cap is a process of programmed cell-cell separation and hydrolase genes such as AtCel5 are likely to be involved.

Example 13

Characterization of *Arabidopsis* Root Cap Using AtCel5 Expression

Given the unique pattern of expression, Applicants used AtCel5-GUS expression to examine root cap sloughing in *Arabidopsis*. Microscopic examination of a shedding root tip revealed that separation involved several tiers of cells that remained intact as they separated from the root tip. In microscopic examination, Applicants observed the stained root tip after they attempted to detach a stained root cap manually with a thin brush. The root cap remained mostly intact and still attached to the center of the root tip, while the cells at the side of the root cap were detached. This would suggest that the side of the root cap loosens and separates first while the center of the root cap separates last. Applicants observed that GUS staining was considerably less in the loosely attached root cap cells than in the cells still firmly adhered to the root. Root cap sloughing has been linked to the ability of the root to penetrate through the soil (Hawes, 1990).

Example 14

Physical Impediment to Growth

To investigate the effect of physical impediment on AtCel5 expression, Applicants grew seeds expressing AtCel5-GUS under conditions of increased resistance during growth by varying the agar content in the MS media. The plates were set at an angle that forced the roots to penetrate the agar. After 10 days of growth, RT-PCR failed to detect any significant changes in AtCel5 transcript accumulation in total root RNA from seedlings growing in different concentrations of agar.

Yet, when AtCel5-GUS staining was performed in the agar plates, without removing the roots from the media, Applicants detected many instances of root cap sloughing in the plates with the maximum percent agar. Applicants also detected carboxymethyl (CM)-cellulase activity in the agar plates where seedlings were growing. Seedlings were grown for 10 days in a media that was supplemented with 0.5% soluble CM-cellulose. Before performing the activity assay, seedlings were removed from the plates, and the imprinted agar was stained for CM-cellulose (0.2% Congo Red). CM-cellulase activity was distinguished as clear patches in the positions where seedlings had been growing. While it is not clear which cellulase is producing this activity in the plates, this is consistent with Applicants' data above suggesting that AtCel5 could be released to the media as cells are shed from the tip.

Example 15

Expression of AtCel5-GUS with Exogenous Auxin and NPA

Applicants observed that GUS activity was greatly reduced compared to controls when seedlings expressing AtCel5-GUS were grown on liquid MS containing IAA (50 µM). Moreover, the roots in treated plants were deformed, bulging and seemed to lack a root cap. When seedlings were removed from the high auxin media and transferred to an auxin-free media, AtCel5-GUS expression was again detected in the tips after a few days (data not shown). To determine if AtCel5 expression was related to the internal IAA concentration, Applicants tested the effect of NPA, a compound that generates an increase in the level of endogenous IAA at the tip by inhibiting the basipetal transport of IAA (Casimiro et al., 2001) and also abolishes the root gravitropic response (Jensen et al., 1998). Thus, when growing on horizontal plates the primary root of control seedlings penetrated the agar while the roots of seedlings growing in plates supplemented with 1 µM NPA grew along the surface of the agar (data not shown). Quantitative determination of GUS activity showed a large decrease in expression in the roots of seedlings grown in agar plates supplemented with 1 µM NPA or 10 µM IAA compared to controls. Thus, high internal concentrations of IAA caused by the inhibition of basipetal auxin transport by NPA and exposure to high exogenous IAA concentrations negatively affect AtCel5 expression.

Example 16

AtCel5 is Ethylene Independent

To determine if AtCel5 expression is affected by ethylene, seedlings were grown for 10 days on MS plates containing 10 µM ACC (which is constitutively converted to ethylene). In the presence of this high concentration of ACC, roots were significantly shorter, more branched and had a considerable increase in root hair density compared to seedlings grown in control plates. Despite these pronounced morphological changes, GUS staining was still observed in the root cap in both cases. Similarly, RT-PCR showed no significant changes in AtCel5 transcript between roots of control and ACC treated seedlings when normalized to the transcript level of KOR, a membrane endo-1,4-β-D-glucanase that is highly expressed in roots and not regulated by ethylene (Nicol et al., 1998). After 10 days on ACC plates, growth was stalled and AtCel5-GUS expression disappeared, however, growth resumed and staining reappeared at the tips when seedlings were transferred to fresh media without ACC (data not shown).

Example 17

AtCel5 is Down-Regulated by Exogenous ABA

Previous studies by (Brigham et al., 1998) have shown the essential role of water in border cell separation; and thus, Applicants examined the effect of water stress on root cap sloughing. During water stress the internal content of ABA increases (Zeevaart and Creelman, 1988), and thus it is possible to mimic aspects of the response to water stress by exposing plant tissues to high exogenous ABA concentrations. Table 1 includes the results of two independent experiments where GUS activity was quantified fluorometrically and compared between control and ABA treated seedlings. In both experiments, AtCel5 expression was reduced by almost half after 24 hour ABA treatment.

Example 18

T-DNA Knockout Mutant for AtCel5

A T-DNA insertion mutant line for the AtCel5 gene was obtained from the Salk collection (Alonso et al., 2003). In this line, the T-DNA is inserted in the AtCel5 coding region, 160 bases downstream from the last exon. Since this is the exon that bears the catalytic signature (position 210 bp), it was expected that the insertion would either completely abolish AtCel5 gene expression, or at least, interrupt gene expression to generate a shorter transcript and an inactive enzyme. Using a gene-specific primer and a T-DNA border primer, a homozygous cel5 mutant was identified. Total RNA from cel5 and wild-type roots, (10 days post-germination) were used as templates for RT-PCR. No AtCel5 transcript was detected in cel5. Nevertheless, when grown in soil, cel5 displayed no observable differences with wild-type plants in terms of overall plant height, size, seed production and response to gravity. Applicants also measured the root length of wild-type and mutant seedlings (7 days post-germination) growing in MS agar media (control) or media supplemented with 4% mannitol or 100 mM NaCl which negatively affects root growth. Both wild type and mutant responded to the treatment but showed no significant differences in their responses (data not shown).

TABLE 1

AtCel5-GUS expression is modulated by ABA.

| | Relative activity[1] | |
| --- | --- | --- |
| | Experiment number 1 | Experiment number 2 |
| Control roots | 1.00 ± 0.06 | 1.00 ± 0.04 |
| ABA roots | 0.53 ± 0.04 | 0.42 ± 0.06 |

[1]Transgenic AtCel5-GUS seedlings at 7 days post-germination (experiment #1) and 10 days post germination (experiment #2) were overlaid for 24 hours with either 10 ml of sterile water (control) or 10 ml of 100 µM ABA solution as described in Materials and methods. Roots were collected and analyzed fluorometrically for GUS activity. The activity (fitted slope ± standard error) in roots of ABA treated seedlings is expressed relative to the activity in controls.

Example 19

AtCel5 and AtCel3 are Paralogs

A large segment of the upper arm of chromosome 1 of the *Arabidopsis* genome, which includes the AtCel5 gene, is duplicated in the lower arm of the same chromosome. The paralog of the AtCel5 gene in the duplicated region was identified as AtCel3/At1g71380, GenBank Accession number U17888, BAC F26A9-24. The amino acid alignment (Corpet, 1988) of both genes showed 87.4% identity and after removing the predicted signal peptide the identity increased to 89.1%. To detect AtCel3 expression by RT-PCR, gene specific primers were designed and tested for specificity using AtCel5 cDNA (AV540005) and genomic DNA as templates. The AtCel3 primers amplified the expected size fragment on genomic DNA template but amplification on AtCel5 cDNA template failed. In contrast, AtCel5 primers amplified the expected fragments in both templates. Once the specificity was confirmed, AtCel3 expression was analyzed in wild-type *Arabidopsis* roots by RT-PCR. Applicants observed that AtCel3 is also expressed in roots, but at a slightly lower level of transcript accumulation than AtCel5.

Example 20

Root Cap Retention Assay

Since expression of AtCel5-GUS is specific to the root cap, Applicants compared the root cap cells of mutant and wild-type plants. After microscopic examination of many root tips from mutant and wild-type plants, Applicants noticed that the root of the mutant forms a root cap and sheds root cap cells just like the root of wild type but sloughing appeared to be less efficient in the mutant. Therefore, Applicants analyzed the retention of the root cap cells after removal of roots from the agar media. Seedlings were grown for 10 days on agar blocks oriented so that the roots were forced to penetrate the agar. At this point the root had grown more than 1 cm into the agar. After 10 days, the seedlings were pulled straight up from the agar and the root tips were examined microscopically. In wild-type root tips, the stress resulting from the removal from the agar usually detached the root cap (66% of cases) or left few tiers of cells loosely attached at the center of the tip (33% of cases). In contrast, the root cap was usually still attached to the root tip of the mutant (69% of cases). Similar results were obtained using a slightly different approach where seedlings of wild type and mutant were lifted from a paper substrate. Seedlings were grown using a modification of the vertical mesh technique (VMT) described by Murphy and Taiz (1995). The modified VMT consisted of a paper (GB002, Schleicher and Schuell)-glass plate assembly, without the nylon membrane, mounted vertically within a Magenta jar containing 50 ml of liquid growth medium. Sterile seeds were set on a row 1 cm below the top of the Wet paper and germinated under the same light conditions as the agar plates.

After 10 days, the paper-glass plate assembly was set horizontally on the bench, seedlings were lifted from the paper and the root tips were examined microscopically. Using this technique, which resulted in a more gentle pulling, Applicants observed that the wild type had only a few tiers of root cap cells loosely attached at the center of the tip and the sides of the cap were flaring out, whereas the mutant retained the root cap in most cases. In addition, Applicants analyzed the root tips of both control and mutant by scanning electron microscopy, which required sequential ethanol washes and high pressure critical drying prior to the observation. The high-pressure treatment usually resulted in complete removal of the root cap in the wild type, but some material was often observed (>50% cases) in SEMs of the cel5 mutant root tips. These results indicate that there is more sloughing in the wild type compared to cel5 mutant.

REFERENCES

Alonso, J. M., Stepanova, A. N., Leisse, T. J., Kim, C. J., Chen, H., Shinn, P., Denise K. S., Zimmerman, J., Barajas, P., Cheuk, R., Gadrinab, C., Heller, C., Jeske, A., Koesema, E., Meyers, C. C., Parker, H., Prednis, L., Ansari, Y., Choy, N., Deen, H., Geralt, M., Hazari, N., Hom, E., Karnes, M., Mulholland, C., Ndubaku, R., Schmidt, I., Guzman, P., Aguilar-Henonin, L., Schmid, M., weige, D., Carter, D. E., Marchand, T., Risseeuw, E., Brogden, D., Zeko, A., Crosby, W. L., Berry, C. C. and Ecker, J. R. 2003. Genome-wide insertional mutagenesis of *Arabidopsis thaliana*. Science 301: 653-657.

Bengough, A. and Mckenzie, B. 1997. Sloughing of root-cap cells decreases the frictional resistance to maize root growth. J. Exp. Bot. 48: 885-893.

Bent, A. F. 2000. *Arabidopsis* in planta transformation: uses, mechanisms, and prospects for transformation of other species. Plant Physiol. 124: 1540-1547.

Birnbaum, K., Shasha, D. E., Wang, J. Y., Jung, J. W., Lambert, G. M., Galbraith, D. W. and Benfey, P. N. 2003. A gene expression map of the *Arabidopsis* root. Science 302: 1956-1960.

Borderies, G., Jamet, E., Lafitte, C., Rossignol, M., Jauneau, A., Boudart, G., Monserrat, B., Esquarreed-Tugaye, M.-T., Bouder, A. and Pont-Lezica, R. 2003. Proteomics of loosely bound cell wall proteins of *Arabidopsis thaliana* cell suspension cultures: a critical analysis. Electrophoresis 24: 3421-3432.

Brigham, L., Woo, H., wen, F. and Hawes, M. 1998. Meristem-specific suppression of mitosis and a global switch in gene expression in the root cap of pea by endogenous signals. Plant Physiol. 118: 1223-1231.

Casimiro, I., Marchant, A., Bhalerao, R. P., Beeckman, T., Dhooge, S., Swarup, R., Graham, N., Inzé, D., Sandberg, G., Pedro J. Casero and Bennett, M. 2001. Auxin transport promotes *Arabidopsis* lateral root initiation. Plant Cell 13: 843-852.

Corpet, F. 1988. Multiple sequence alignment with hierarchical clustering. Nucl. Acids Res. 16: 10881-10890.

del Campillo, E. 1999. Multiple endo-1,4-b-D-glucanase (cellulase) genes in *Arabidopsis*. Curr. Top. Dev. Biol. 46: 39-61.

del Campillo, E. and Bennett, A. B. 1996. Pedicel break-strength and cellulase gene expression during tomato flower abscission. Plant Physiol. 111: 813-820.

del Campillo, E. and Lewis, L. 1992. Occurrence of 9.5 cellulase and other hydrolases in flower reproductive organs undergoing major cell wall disruption. Plant Physiol. 99: 1015-1020.

DiDonato, R. J., Arbuckle, E., Buker, S., Sheets, J., Tobar, J., Totong, R., Grisafi, P., Fink, G. R. and Celenza, J. L. 2004. *Arabidopsis* ALF4 encodes a nuclear localized protein required for lateral root formation. Plant J. 37: 340-353.

Gonzalez-Bosch, C., Campillo, E. D. and Bennett, A. B. 1997. Immunodetection and characterization of tomato endo-[beta]-1,4-glucanase cell protein in flower abscission zones. Plant Physiol. 114: 1541-1546.

Hawes, M. 1990. Living plant cells released from the root cap: a regulator of microbial populations in the rhizosphere? Plant Soil 129: 19-27.

Hawes, M. C., Brigham, L. A., wen, F., Woo, H. H. and Zhu, Y. 1998. Function of root border cells in plant health: pioneers in the rhizosphere. Annu. Rev. Phytopathol. 36: 311-327.

Henrissat, B. 1991. A classification of glycosyl hydrolases based on amino-acid sequence similarities. Biochem. J. 280: 309-316.

Henrissat, B. and Bairoch, A. 1993. New families in the classification of glycosyl hydrolases based on amino acid sequence similarities. Biochem. J. 293: 781-788.

Henrissat, B. and Bairoch, A. 1996. Updating the sequence-based classification of glycosyl hydrolases. Biochem. J. 316: 695-696.

Higo, K., Ugawa, Y., Iwamoto, M. and Korenaga, T. 1999. Plant cis-acting regulatory DNA elements (PLACE) database. Nucleic Acids Res. 27: 297-300.

Iijima, M., Higuchi, T., Barlow, P. and Bengough, A. 2003. Root cap removal increases root penetration resistance in maize (*Zea mays L*). J. Exp. Bot. 54: 2105-2109.

Iwasaki, T., Yamaguchi-Shinozaki, K. and Shinozaki, K. 1995. Identification of a cis-regulatory region of a gene in *Arabidopsis thaliana* whose induction by dehydration is mediated by abscisic acid and requires protein synthesis. Mol. Gen. Genet. 247: 391-398.

Jaglo-Ottosen, K. R., Gilmour, S. J., Zarka, D. G., Schabenberger, O. and Thomashow, M. F. 1998. *Arabidopsis* CBF1 overexpression induces COR genes and enhances freezing tolerance. Science 3: 104-106.

Jefferson, R. A., Kavanagh, T. A. and Bevan, M. W. 1987. GUS fusions: b-glucuronidase is a sensitive and versatile fusion marker in higher plants. EMBO J. 6: 3901-3907.

Jensen, P. J., Hangarter, R. P. and Estelle, M. 1998. Auxin transport is required for hypocotyl elongation in light-grown but not dark-grown *Arabidopsis*. Plant Physiol. 116: 455-462.

Kalaitzis, P., Hong, S. B., Solomos, T. and Tucker, M. L. 1999. Molecular characterization of a tomato [Lycopersicon esculentum]endo-beta-1,4-glucanase gene expressed in mature pistils, abscission zones and fruit. Plant Cell Physiol.: 905-908.

Lashbrook, C. C., Gonzalez-Bosch, C. and Bennett, A. B. 1994. Two divergent Endo-[beta]-1,4-glucanase genes exhibit over-lapping expression in ripening fruit and abscising flowers. Plant Cell 6: 1485-1493.

Laskowski, M., Williams, M., Nusbaum, C. and Sussex, I. M. 1995. Formation of lateral root meristems is a two-stage process. Development 121: 3303-3310.

Lu, G. and Ferl, R. 1995. An *Arabidopsis* cDNA encoding beta-glucanase. Plant Mol. Biol. 29: 883.

Milioni, D., Sado, P.-E., Stacey, N. J., Domingo, C., Roberts, K. and McCann, M. 2001. Differential expression of cell-wall-related genes during the formation of tracheary elements in the Zinnia mesophyll cell system. Plant Mol. Biol. 47: 221-238.

Milioni, D., Sado, P.-E., Stacey, N. J., Roberts, K. and McCann, M. 2002. Early gene expression associated with the commitment and differentiation of a plant tracheary element is revealed by cDNA-amplified fragment length polymorphism analysis. Plant Cell 14: 2813-2824.

Miyasaka, S. and Hawes, M. 2001. Possible role of root border cells in detection and avoidance of aluminum toxicity. Plant Physiol. 125: 1978-1987.

Moseyko, N., Zhu, T., Chang, H.-S., Wang, X. and Feldman, L. J. 2002. Transcription profiling of the early gravitropic response in *Arabidopsis* using high-density oligonucleotide probe microarrays. Plant Physiol 130: 720-728.

Murashige, T. and Skoog, F. 1962. A revised medium for rapid growth and bioassays with tobacco tissue culture. Physiol. Plant. 15: 473-497.

Murphy, A. and Taiz, L. 1995. A new vertical mesh transfer technique for metal-tolerance studies in *Arabidopsis*. Ecotypic variation and copper-sensitive mutants. Plant Physiol. 108: 29-38.

Nicol, F., His, I., Jauneau, A., Vernhettes, S., Canut, H. and Höfte, H. 1998. A plasma membrane-bound putative endo-1,4-b-D-glucanase is required for normal wall assembly and cell elongation in *Arabidopsis*. EMBO 17: 5563-5576. 322

Thoma, S. L., Glass, T., Most, A. and Patterson, S. E. 2003. Analysis of an abscission-associated cellulase in *Arabidopsis*. 14th International Conference on *Arabidopsis* Research, Madison, Wis.

Tucker, M., Sexton, R., del Campillo, E. and Lewis, L. 1988. Bean abscission cellulase: characterization of a cDNA clone and regulation of gene expression by ethylene and auxin. Plant Physiol. 88: 1257-1262.

Ulmasov, T., Murfett, J., Hagen, G. and Guilfoyle, T. J. 1997. Aux/IAA proteins repress expression of reporter genes containing natural and highly active synthetic auxin response elements. Plant Cell 9: 1963-1971.

wen, F., Zhu, Y. and Hawes, M. 1999. Effect of pectin methylesterase gene expression on pea root development. Plant Cell 11: 1129-1140.

Willats, W. G. T., Willats W. G. T., McCartney L., Steele-King C. G., Marcus S. E., Mort A., Huisman M., van Alebeek G.-J., Schols H. A., Voragen A. G. J., Le Goff A., Bonnin E., Thibault J.-F. and J. P., K. 2004. A xylogalacturonan epitope is specifically associated with plant cell detachment. Planta 218: 673-681.

Zeevaart, J. A. D. and Creelman, R. A. 1988. Metabolism and physiology of abscisic acid. Annu. Rev. Plant. Physiol. 39: 438-473. 323

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A construct comprising an isolated root cap promoter having the polynucleotide sequence of SEQ ID NO: 1 wherein said promoter is operably linked to an exogenous transcribable polynucleotide sequence.

2. The construct of claim 1, wherein said transcribable polynucleotide sequence encodes for a protein selected from the group consisting of β-glucuronidase (GUS), green fluorescent protein (GFP), luciferase (LUC), a protein that confers antibiotic resistance and a protein that confers herbicide resistance.

3. The construct of claim 2, wherein the transcribable polynucleotide sequence encodes for GUS.

4. The construct of claim 1, wherein said transcribable polynucleotide sequence encodes a protein selected from the group consisting of antifungal proteins, antibacterial proteins, antiparasitic proteins, antiviral proteins, anti-nematode proteins and growth factors.

5. The construct of claim 4, wherein the protein protects a plant root from infection.

6. The construct of claim 4, wherein the growth factor promotes root growth.

7. The construct of claim 1, wherein the transcribable polynucleotide sequence is selected from genes that modulate nutrient uptake, modulate toxin uptake, modulate water uptake, modulate sugar production, modulate starch production, or modulate oil production.

8. The construct of claim 1, wherein the transcribable polynucleotide sequence encodes an endo-1,4-beta-D-glucanase.

9. A transgenic plant comprising the construct of claim 1.

10. The transgenic plant of claim 9, wherein said plant is selected from the group consisting of *Arabidopsis*, tomato, tobacco, potato, beets, carrots and corn.

11. The transgenic plant of claim 9, wherein said construct comprises the transcribable polynucleotide sequence that confers altered root cap cell sloughing to said transgenic plant.

12. A seed of the transgenic plant of claim 9, wherein the seed comprises said construct.

13. A cell of the transgenic plant of claim 9.

14. The cell of claim 13, wherein the cell is a root cap cell.

15. An expression vector comprising the construct of claim 1.

* * * * *